United States Patent
Patil et al.

(10) Patent No.: US 11,332,437 B2
(45) Date of Patent: May 17, 2022

(54) UREA PRODUCTION WITH MULTIPLE EVAPORATORS

(71) Applicant: STAMICARBON B.V., Sittard (NL)

(72) Inventors: Rahul Patil, Maastricht (NL); Petrus Anna Maria Robertus Simons, Schimmert (NL); Branislav Manic, Maastricht (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 17/424,958

(22) PCT Filed: Dec. 30, 2020

(86) PCT No.: PCT/NL2020/050826
§ 371 (c)(1),
(2) Date: Jul. 22, 2021

(87) PCT Pub. No.: WO2021/137701
PCT Pub. Date: Jul. 8, 2021

(65) Prior Publication Data
US 2022/0089529 A1    Mar. 24, 2022

(30) Foreign Application Priority Data
Dec. 30, 2019    (EP) ..................................... 19220084

(51) Int. Cl.
*C07C 273/16*    (2006.01)
*B01D 5/00*    (2006.01)
(Continued)

(52) U.S. Cl.
CPC ............ *C07C 273/16* (2013.01); *B01D 5/006* (2013.01); *B01D 5/009* (2013.01); *B01D 5/0054* (2013.01);
(Continued)

(58) Field of Classification Search
USPC ................... 159/24.3, 47.2; 203/42, 73, 80; 202/185.2, 205; 564/73
See application file for complete search history.

(56) References Cited

U.S. PATENT DOCUMENTS 4,256,662 A    3/1981    Gorlovsky et al.
4,821,524 A    4/1989    Kostyal et al.
(Continued)

FOREIGN PATENT DOCUMENTS

CN    203578057 U    5/2014
EP    2192099 A1    6/2010
(Continued)

OTHER PUBLICATIONS

International Search Report and Written Opinion in corresponding International Patent Application No. PCT/NL2020/050824 dated Mar. 23, 2021. 9 pages.

(Continued)

*Primary Examiner* — Nina Bhat
(74) *Attorney, Agent, or Firm* — Leason Ellis LLP

(57) ABSTRACT

A urea production process which includes and a synthesis section, a recovery section and evaporation section and a finishing section wherein the evaporation section includes a first evaporator and downstream thereof a second evaporator for urea solution. The second evaporator operates a lower pressure than the first evaporator to provide a urea melt and second vapor, solidifying the urea melt in a finishing section to provide a solid urea produce and off gas, scrubbing the off gas followed by condensing to produce a first condensate and second condensate; supplying the first condensate to a wastewater treatment section and supply the second condensate to the scrubber wherein the second condensate is used as a scrub liquid in the scrubber.

14 Claims, 2 Drawing Sheets

(51) Int. Cl.
  B01D 53/78 (2006.01)
  C02F 1/02 (2006.01)
  C02F 1/20 (2006.01)
  B01D 53/54 (2006.01)
  C02F 103/36 (2006.01)
  B01D 1/00 (2006.01)

(52) U.S. Cl.
  CPC ............ B01D 53/54 (2013.01); B01D 53/78 (2013.01); C02F 1/025 (2013.01); C02F 1/20 (2013.01); B01D 1/0029 (2013.01); C02F 2103/36 (2013.01)

(56) References Cited

U.S. PATENT DOCUMENTS

| | | | |
|---|---|---|---|
| 5,744,009 A * | 4/1998 | Singh | C07C 273/16 202/205 |
| 7,687,041 B2 | 3/2010 | Singh | |
| 9,458,098 B2 * | 10/2016 | Mennen | B01J 10/00 |
| 10,370,326 B2 * | 8/2019 | Puci | C07C 273/16 |
| 10,486,125 B2 * | 11/2019 | Scotto | C07C 273/16 |
| 10,882,820 B2 * | 1/2021 | Mostert | C07C 273/16 |
| 2009/0084149 A1 | 4/2009 | Van Der Werf et al. | |
| 2011/0229394 A1 * | 9/2011 | Niehues | C05C 9/005 422/187 |
| 2014/0206902 A1 | 7/2014 | Mennen | |
| 2015/0133689 A1 * | 5/2015 | Potthoff | B01D 1/00 422/187 |
| 2015/0133690 A1 | 5/2015 | Mennen et al. | |
| 2016/0184758 A1 * | 6/2016 | Soons | C07C 273/02 118/69 |
| 2017/0312717 A1 * | 11/2017 | Scotto | B01J 2/003 |
| 2018/0326345 A1 * | 11/2018 | Doherty | B01D 47/05 |
| 2019/0185422 A1 * | 6/2019 | Pustjens | B01D 5/0054 |
| 2021/0024460 A1 * | 1/2021 | Franzrahe | B01D 9/0027 |

FOREIGN PATENT DOCUMENTS

| | | |
|---|---|---|
| EP | 3020702 A1 | 5/2016 |
| GB | 1528051 | 10/1978 |
| WO | 2010060535 A1 | 6/2010 |
| WO | 2013165245 A1 | 11/2013 |
| WO | 2013165246 A1 | 11/2013 |
| WO | 2014188371 A1 | 11/2014 |
| WO | 2021/137699 A1 | 7/2021 |
| WO | 2021/137700 A1 | 7/2021 |

OTHER PUBLICATIONS

International Preliminary Report on Patentability in corresponding International Patent Application No. PCT/NL2020/050824 dated Jun. 29, 2021. 11 pages.
International Search Report and Written Opinion in corresponding International Patent Application No. PCT/NL2020/050825 dated Mar. 23, 2021. 9 pages.
International Search Report and Written Opinion in corresponding International Patent Application No. PCT/NL2020/050826 dated Mar. 10, 2021. 11 pages.
International Preliminary Report on Patentability in corresponding International Patent Application No. PCT/NL2020/050826 dated Jun. 17, 2021. 12 pages.
Meessen. Ullmann's Encyclopedia of Industrial Chemistry. "Urea." Wiley-VCH Verlag GmbH & Co. KGaA, Weinheim (2010). 10.1002/14356007.a27_333.pub2. 39 pages.
Mo Author. "Urea Synthesis: A Status Report—I." Nitrogen No. 185, May-Jun. 1990. pp. 22-29.
Potthoff. "Innovative Ammonia Emission Reductions." Nitrogen+Syngas 294, Jul.-Aug. 2008, pp. 39-41. XP-002525996. 4 total pages.
Van Der Zande. "Zero waste urea production." Fertilizer Focus, Mar.-Apr. 2018. 3 pages.
Non-Final Office Action for related U.S. Appl. No. 17/424,940, dated Feb. 2, 2022. 10 pages.

* cited by examiner

UREA PRODUCTION WITH MULTIPLE EVAPORATORS

CROSS-REFERENCE TO RELATED PATENT APPLICATIONS

This application is a U.S. National Stage Application under 35 U.S.C. § 371 of International Patent Application No. PCT/NL2020/050826 filed Dec. 30, 2020, which claims the benefit of priority of European Patent Application No. EP 19220084.8 filed Dec. 30, 2019, both of which are incorporated by reference in their entireties. The International Application was published on Jul. 8, 2021, as International Publication No. WO 2021/137701 A1.

FIELD

The invention pertains to the production of urea. Particularly, the invention pertains to the production of urea melt in conjunction with urea finishing into solid urea products.

INTRODUCTION

The invention pertains to a urea production process and plant involving a synthesis section, a recovery section, an evaporation section, and a finishing section. The synthesis section of the process and plant of the invention is a high pressure synthesis section for reacting $NH_3$ and $CO_2$ under urea forming conditions to give a urea synthesis solution comprising urea, water, ammonia and ammonium carbamate. In the urea formation reaction, one molecule water is formed for each molecule urea. For producing solid urea, this water needs to be removed. The recovery section has an inlet for urea synthesis solution and an outlet for urea solution. In the recovery section ammonia and ammonium carbamate are at least in part removed from the urea solution. A carbamate solution is recycled from the recovery section to the synthesis section to recycle $NH_3$ and $CO_2$ feed. The recycle solution preferably has a low relative water content as water is detrimental to the urea yield.

The evaporation section has an inlet for urea solution and an outlet for urea melt.

The finishing section has an inlet for urea melt and an outlet for solid urea product and off-gas. The finishing section is adapted for solidifying the urea. The solid urea product comprises urea and optionally other solid components such as ammonium salts. In the present invention, the finishing section is for instance a prilling tower, a granulator, or a pastillation unit. The granulator is for instance a fluidized bed or a spouted bed granulator. A prilling tower as optionally used in the present invention comprises for instance spray nozzles for urea melt arranged at the top of the prilling tower. In operation, sprayed urea droplets solidify during their fall. The prilling tower is for instance a forced draft, induced draft, or natural draft pulling tower. The pastillation unit as optionally used in the present invention is for instance a Sandvik® Rotoform® apparatus. The optional pastillation unit comprises for instance a droplet depositor for depositing urea melt droplets arranged above a steel belt cooler.

The off-gas from the finishing section of the invention comprises air, urea dust and $NH_3$. The off-gas is sent to a scrubber where it is treated with scrub liquid to give cleaned off-gas and utilized scrub liquid.

The evaporation section used in the present invention comprises a first evaporator and downstream thereof (for urea solution) a second evaporator. The second evaporator preferably operates at a lower pressure than the first evaporator, e.g. preferably at least 10 kPa lower. The first and second evaporator are each heat exchangers, preferably are each shell-and-tube heat exchangers using e.g. steam as heating fluid. Preferably, urea solution is supplied in the tubes and heating fluid in the shell. The first and second evaporator both operate at an absolute pressure of less than 100 kPa (1.0 bar) or less than 50 kPa (0.5 bar) at the process side.

In some embodiments, the first evaporator of the present invention operates at an absolute pressure of 10 to 80 kPa (0.1-0.8 bar) on the process side (for urea solution), e.g. 15 to 50 kPa. In some embodiments, the second downstream evaporator operates at an absolute pressure of 1.0 to 20 kPa, e.g. 1.0 to 10 kPa (for urea solution). Preferably with these low pressures the urea melt from the second evaporator comprises less than 2.0 wt. % moisture, such as less than 0.1 wt. % moisture. Such urea melts with low moisture are for instance used in the present invention for preferred embodiments wherein the finishing section is a prilling tower or a granulator.

Preferably the absolute pressure in the first evaporator is at least 2 times the absolute pressure in the second evaporator in the present invention.

Water vapors obtained as a result of evaporation, will inevitably comprise residual ammonia and carbon dioxide, as well as possibly entrained urea. It is desired that such residual reactants and entrained urea are not wasted. Also, it is desired to be able to use purified water as a utility in a steam circuit in the urea plant, and/or as a scrubbing liquid for a scrubber of a finishing section of the urea plant. Vapor condensate obtained from evaporation is therefore sent (as process condensate) to a waste water treatment section (also known as water-purification section). Therein ammonia and carbon dioxide are removed and recirculated to urea synthesis. This includes ammonia and carbon dioxide obtained from the entrained urea, which in the waste water treatment section is effectively hydrolysed.

FIG. 1 shows a reference urea production process not according to the invention. The evaporation section (EV) of the urea plant comprises at least a first evaporator (EV1) which has an inlet for a first urea solution (U1), an outlet for concentrated urea solution (U2), and a first vapor outlet (V1). The vapor outlet is connected to a first condenser (C1) which used cooling water (cw). The first condenser (C1) has an outlet for condensate (PC1) connected to a wastewater treatment section (WWT), and an outlet for vapor (V3) typically connected to an ejector (Ej1) for maintaining vacuum. The evaporation section further comprises a downstream second evaporator (EV2). The second evaporator has an outlet for urea melt (UM), an inlet for the concentrated urea solution (U2) and a vapor outlet (V2) connected to a second condenser (C2) typically via a booster ejector (BEj) using steam (S1). The second condenser (C2) uses cooling water. The second condenser has an outlet for (fourth) vapor (V4) connected to a second ejector (Ej2) for maintaining vacuum (both ejectors can be combined). The second condenser (C2) further has an outlet for condensate (PC2) connected to the wastewater treatment section (WWT).

Example urea plants with such an evaporation section comprising two evaporators in series, and example finishing sections are described in Ullmann's Encyclopedia of Industrial Chemistry, chapter Urea (2010). The document illustrates a self-stripping process, the first and second evaporation heater both have a vapor outlet connected to a condenser. The condenser has an outlet connected to a wastewater treatment section.

Invariably condensate from an evaporation section contains urea and ammonia. For instance, the process condensate produced from the evaporation section of a urea plant contains 3 to 8 wt. % ammonia and 0.2 to 2 wt. % urea, and typically also $CO_2$.

Typically condensate from an evaporation section is treated in a waste water treatment (WWT) (also known as process condensate treatment section), for instance with a hydrolyser and a desorber. The desorber is e.g. based on steam stripping. In an example WWT section a hydrolyser is used for hydrolysis of urea using steam at 170° C. to 230° C. as well as a desorber based on steam stripping at 1 to 5 bar. The operation of a WWT section is very energy consuming.

US2015/0133690 discusses that the process condensate treatment of a urea plant requires valuable steam, i.e. is energy intensive, and that it is desired to minimize the amount of steam used in this section.

H. van der Zande, "Zero waste urea production", Fertilizer Focus March-April 2018 schematically shows a urea plant with a urea melt plant having an outlet, connected to a granulation plant, the granulation plant having an outlet for gas connected to a scrubber using acidic solution. The urea melt plant has an outlet for wastewater connected to a WWT. The WWT comprises a hydrolyser and a desorber. The hydrolyser uses counter-current contact with steam, the desorber uses steam stripping. The vapors from the WWT are condensed in a carbamate condenser, the resulting liquid stream is sent to recirculation.

SUMMARY

The invention pertains in a first aspect to a urea production process comprising: concentrating urea solution in a first evaporator of an evaporation section, to give concentrated urea solution and a first vapor; further concentrating said concentrated urea solution from said first evaporator in a second evaporator of said evaporation section, to give a urea melt and second vapor; solidifying said urea melt in a finishing section giving solid urea product and off-gas; scrubbing said off-gas in a scrubber; condensing said first vapor in a first condenser to give a first condensate; condensing said second vapor in a second condenser to give a second condensate; supplying said first condensate to a wastewater treatment (WWT) section; and supplying said second condensate to said scrubber. The first and second condensate are transported separately from each other. In particular, the first and second condensate are not mixed. The first condensate and the second condensate are in particular separate liquid streams and are transported in separate liquid flow connections.

The invention also pertains to a urea production plant comprising an evaporation section, a finishing section, a wastewater treatment section, and a scrubber, wherein the evaporation section comprises a first evaporator and downstream thereof a second evaporator, and a first condenser and a second condenser, wherein said first evaporator comprises an inlet for urea solution, an outlet for concentrated urea solution and an outlet for a first vapor; said second evaporator comprises an inlet for said concentrated urea solution, an outlet for urea melt and an outlet for second vapor; said finishing section comprises an inlet for said urea melt, an outlet for solid urea product and an outlet for off-gas and is configured for solidifying said urea melt into said solid urea product; said scrubber comprises an inlet for said off-gas and is configured for scrubbing said off-gas using scrub liquid; said first condenser comprises an inlet for said first vapor and an outlet for a first condensate; said second condenser comprises an inlet for said second vapor and an outlet for a second condensate; said wastewater treatment section comprises an inlet for said first condensate, and the plant comprises a first connection for said first condensate from said first condenser to said wastewater treatment section and a second connection for said second condensate from said outlet of said second condenser directly to an inlet of said scrubber; wherein in particular said first connection and said second connection are separate from each other. The first and second connection in particular are configured for transporting the first condensate and the second condensate separately from each other.

Figure 1:
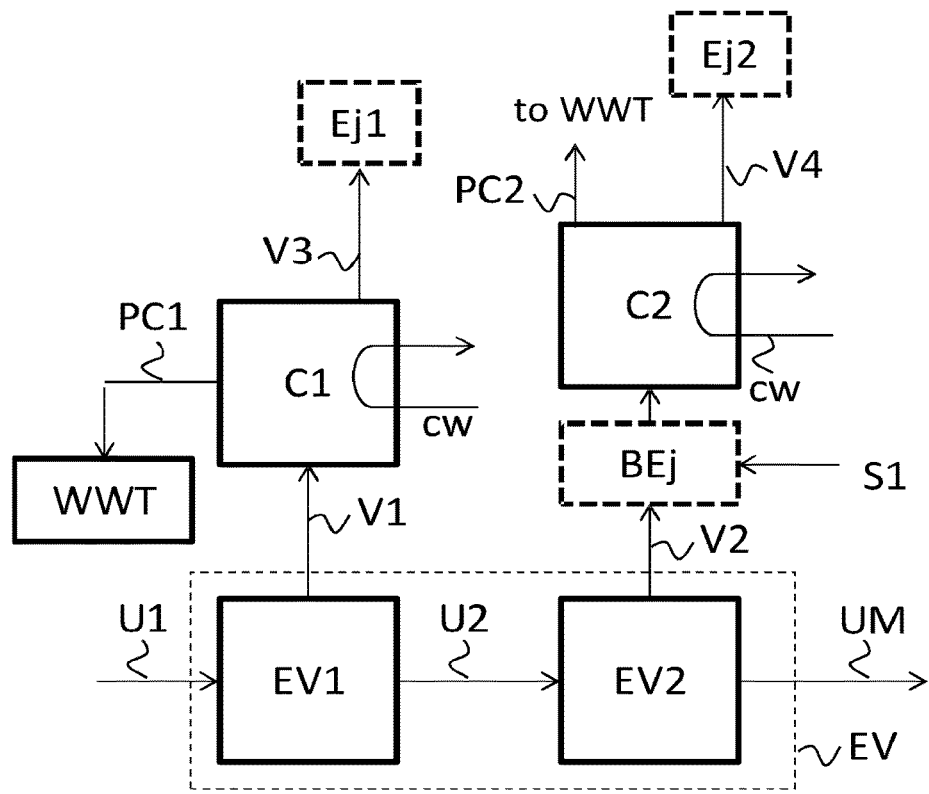
FIG. 1 schematically illustrates a reference process.

The figures are illustrative only and do not limit the invention.

DETAILED DESCRIPTION

The present invention provides for a very energy efficient urea production process and plant by sending condensate obtained in the condenser of the downstream second evaporator of the evaporation section to the scrubber where off-gas from the finishing section is treated. In addition, condensate obtained in the condenser of the upstream first evaporator is supplied to a wastewater treatment section. In this way the load on the WWT is reduced, thereby providing for improved energy efficiency. The improved energy efficiency yields a reduced consumption of high pressure steam and/or an increased export of low pressure steam. The relatively smaller amount of water evaporated in the second evaporator gives a relatively smaller amount of vapor such that the resulting condensate can advantageously be treated in the scrubber. Preferably the off-gas from the finishing section is relatively hot and dry contributing to the evaporation of sufficient water and removal of water vapor with the cleaned off-gas from the scrubber.

As used herein, for process streams (in particular urea solution), high pressure (HP) is at least 100 bara, e.g. 100 to 200 bara or 110-160 bara, medium pressure (MP) is 20-60 bara, low pressure (LP) is 4-10 bara. These pressure ranges are for process solutions and not necessarily the same for heating fluids such as steam. For steam, high pressure (HP) means 18-40 bara, preferably 20-25 bara medium pressure (MP) means 8-12 bara, preferably 9-10 bara and low pressure (LP) means 3-6 bara, preferably 4-5 bara. The abbreviation "bara" means bar absolute.

The inventive process can be described as a urea production process or a process for producing a urea melt or a process for concentrating urea solution. The urea production process preferably comprises an initial urea synthesis step in a high pressure urea synthesis section to give a urea synthesis solution, e.g. as discussed hereinabove. The synthesis section comprises a high pressure reactor and preferably a high pressure stripper and a high pressure carbamate condenser.

The urea production process preferably comprises a step of removing ammonia and ammonium carbamate from the urea synthesis solution in a recovery section to give a urea solution. The recovery section comprises e.g. a low pressure recovery section or a medium pressure recovery section with a downstream low pressure urea recovery section. The recovery section(s) comprises e.g. a decomposer (such as a heat exchanger) for heating urea solution, having a first outlet for gas and a second outlet for urea solution, and a carbamate condenser for condensing said gas to form a recycle carbamate solution typically at low or medium pressure.

The evaporation section comprises the first evaporator and the second evaporator as discussed. The urea solution as received by the first evaporator comprises e.g. 10 to 40 wt. % water and e.g. about 70 wt % urea, Preferably, the first evaporator reduces the water content by at least 10 wt. % percentage points, e.g. from 40 wt. % to 30 wt. %. Preferably the concentrated urea solution provided by the first evaporator comprises 5 to 20 wt % water. Preferably the concentrated urea solution received by the second evaporator comprises 5 to 20 wt. % water and for instance about 90 wt % urea (including biuret). Preferably, the amount of water vapor formed in the first evaporator is at least 2 times the amount of water vapor formed in the second evaporator. The first evaporator is e.g. a heat exchanger using steam as heating fluid for indirect heat exchange through a wall with the urea solution, wherein the steam is e.g. MP steam or LP steam.

The first evaporator can for instance also be a heat exchanger comprising a first and a second compartment separated by a heat exchanging wall (such as a tube-and-shell heat exchanger), wherein in the first compartment the urea solution is heated and wherein in the second compartment $CO_2$ and $NH_3$ are condensed into ammonium carbamate. The carbamate condensation reaction is exothermic. The condensation is carried out for instance at medium pressure, e.g. 1.8-3.0 MPa (18 to 30 bara). The first heat exchanger can for instance be provided by a condenser-evaporator. The gas stream comprising $CO_2$ and $NH_3$ received by the condenser-evaporator originates for instance from a separator or dissociator. The separator or dissociator is operated at MP. The separator or dissociator receives e.g. urea synthesis solution from a HP reactor or stripped urea solution from the HP stripper, preferably after expanding the urea solution to MP. A dissociator is e.g. a heat exchanger using steam for promoting the dissociation of carbamate in a urea solution comprising carbamate. The separator is a gas/liquid separator. A background referencing illustrating a urea plant with such a MP condenser-evaporator is WO 2013/165246.

The second evaporator yields a urea melt comprising e.g. 0.10 to 5.0 wt. % water, such as preferably 0.1-0.5 wt. % in case the finishing section is a prilling tower, or 1.0 to 5.0 wt. % water in case the finishing section is a granulator. The second evaporator is e.g. a heat exchanger using steam as heating fluid for indirect heat exchange through a wall with the urea solution, wherein the steam is e.g. MP steam or LP steam.

The first evaporator preferably gives a concentrated urea solution with at least 90 wt. % urea (including biuret), more preferably 92 to 96 wt. % at the outlet. The first evaporator operates e.g. with a temperature of at least 120° C., and/or up to 145° C., preferably 130° C. to 140° C. at the outlet. The first evaporator operates e.g. with a pressure of 20 to 35 kPa at the process side receiving the urea solution. The heat for the first evaporator can be provided e.g. by using steam as heating fluid, or by using heat of condensation of carbamate.

In an embodiment, the second evaporator uses MP steam of e.g. 8-9 bara, providing a urea melt with at least 98.5 wt. % urea including biuret, e.g. less than 1.5 wt. % water. In an embodiment, the second evaporator uses LP steam of e.g. 4-5 bar, providing a urea melt with a water content of at least 1.5 wt. % and typically less than 5 wt. % water. The second evaporator operates e.g. at 130-140° C., in particular at 140° C. and/or at a pressure of less than 15 kPa, e.g. 1-5 kPa or 5-15 kPa. A pressure of 1 to 5 kPa can be used to prepare a urea melt, e.g. at 140° C., with e.g. at least 99.5 wt. % urea including biuret and/or e.g. less than 0.5 wt. % moisture which is suitable for e.g. prilling and pastillation. A pressure of 10 to 15 kPa can be used to prepare a urea melt, e.g. at 140° C., with a moisture content of e.g. 1.0 to 3 wt. %, which is suitable e.g. for fluidized bed granulation. In some embodiments the second evaporator may operate at a pressure of 15-30 kPa, such as 20-30 kPa, e.g. at 135-140° C. to give a urea melt with e.g. 1.0 to 5.0 wt. % moisture which can be used e.g. in certain types of granulation. The preferred and exemplified first and second evaporators are preferably used in combination with each other.

The process involves solidifying the urea melt in a finishing section to give solid urea and off-gas. The solid urea may contain urea and other solid components such as sulphur-containing components. The off-gas includes air, urea dust and $NH_3$, as discussed. The finishing section is for instance a prilling tower, a granulator, or a pastillation apparatus as discussed.

The process involves scrubbing the off-gas in a scrubber. The scrubbing involves contacting the off-gas with a scrub liquid. The scrubber comprises for instance a venturi scrubber. The scrub liquid comprises water. The scrub liquid can be used to remove urea dust. The scrub liquid optionally comprises acid, such as a mineral acid, e.g. nitric acid or sulphuric acid. The optional acid can be used for acid scrubbing to remove or more completely remove $NH_3$. The scrub liquid is e.g. recirculated in the scrubber up to a urea content of e.g. 10-60 wt. %, e.g. 20 to 50 wt. % urea. Preferably utilized scrub liquid is purged from the scrubber. The utilized scrub liquid contains urea. Preferably, the utilized scrub liquid is advantageously supplied to the second evaporator. In this way, urea contained in the second condensate is recycled into the solid urea product rather than hydrolysed. Urea contained in the second condensate is in particular processed separately from the first condensate. This improves the overall urea yield and thereby increases plant capacity.

If the scrub liquid comprises an acid, the utilized scrub liquid comprises an ammonium salt due to the removal of ammonia from at least the off-gas. This ammonium salt solution can be disposed of by supplying the utilized scrub liquid to the evaporation section. A background reference for supplying utilized scrub liquid comprising ammonium salt to an evaporation section of a urea plant is Potthoff, Nitrogen+Syngas 294, p. 39.

In the present invention, if the utilized scrub liquid, optionally containing ammonium salt, is supplied to the evaporation section, it is preferably supplied only to the downstream second evaporator, e.g. by adding the utilized scrub liquid to the concentrated urea solution obtained from the first evaporator. Preferably the utilized scrub liquid is supplied to the evaporation section downstream (for urea solution) of the first evaporator. In this way, no ammonium salts formed in the scrubber (e.g. ammonium nitrate or ammonium sulphate) are introduced in the first evaporator which has a condenser connected to the wastewater treatment section (WWT). This is advantageous to avoid contamination of the water obtained from the WWT. The water from the WWT needs to be very pure because it is used e.g.

in part or entirely as boiler feed water for raising steam. In particular, no part of the second condensate is supplied to the WWT.

The ammonium salts are included in the solid urea product e.g. in an amount of less than 5.0 wt. % and/or at least 0.10 wt. %, such as 1.0-3.0 wt. %. For instance the solid urea product has a nitrogen content of at least 46 wt. % thereby meeting the minimum nitrogen content for urea fertilizer. In this way, the ammonia from the off-gas as well as from the second condensate advantageously contributes to the solid urea product yield in an energy efficient way and without additional water recycle to the urea synthesis.

In an interesting embodiment, the solid urea product comprises one or more additives, for instance in amount of at least 0.010 wt. %, at 0.10 wt. % or at least 1.0 wt. % or at least 5 wt. % or at least 10 wt. %, suitably less than 30 wt. %, based on total weight of additives and total weight of solid urea product. The additive is a compound other than urea and biuret. The additive comprises for instance a micronutrient for plants or animals or a plant nutrient such as a P, S or K compound, such as a sulphate or phosphate salt. The additive is for instance selected from the group consisting of ammonium nitrate, ammonium sulphate, calcium nitrate, di- or mono-ammonium phosphate, potassium nitrate, sodium nitrate, and phosphorus compounds such as potassium phosphate compounds, or potassium compounds such as potassium chloride, potassium nitrate, potassium sulphate, and potassium phosphate compounds. Micronutrients include e.g. iron sulphate, iron oxides, zinc sulfate, iron nitrate, zinc oxide, chelated zinc, chelated iron copper oxide, copper sulfate, copper nitrate, magnesium nitrate, magnesium sulphate, magnesium oxide, selenium sulphate, and selenium oxide, and iodine compounds such as potassium iodide. The individual additives are included for instance in an amount of at least 10 ppm or at least 100 ppm by weight, based on total weight of solid urea product. Preferably the one or more additives include one or more compounds selected from the group consisting of B, Cl, Fe, Mn, Zn, Cu, Mo and Ni. These compounds are used as plant micronutrients.

Preferably the inventive process comprises supplying a liquid stream comprising water and the additive(s), more preferably an aqueous solution comprising the additive(s), to the evaporation section downstream (for urea solution) of the first evaporator. In this way, the additive compounds do not end up in the WWT. Preferably the liquid stream comprising additive(s) is supplied to the second evaporator, e.g. is mixed with the concentrated urea solution in the transport line between the first and second evaporator, or is supplied to an inlet, of the second evaporator. Very advantageously, this allows for mixing an aqueous solution of the additive(s) to the concentrated urea solution and subsequently removing the water (used as solvent for the additives) from the urea solution in the second evaporator. As the vapor from the second evaporator is sent, after condensation, to the scrubber instead of to the WWT, there is no risk of contaminating the WWT. In particular, the second condensate is supplied to the scrubber without any part of said second condensate being supplied to the WWT. For instance, the second condensate is supplied directly to the scrubber. Mixing an aqueous additive solution with a concentrated urea solution is less complicated than adding solid additive to the urea melt downstream of the evaporation section. Moreover mixing solutions contributes to a homogeneous distribution of the additive(s) in the solid urea product. The additive may originate from an external supply, such as in case of micronutrients.

In a particularly preferred embodiment, additives are added to utilized scrub liquid, e.g. in a sump of the scrubber, and the utilized scrub liquid is supplied to the second evaporator as discussed.

In the present invention, the vapor from the downstream second evaporator is condensed in a second condenser to form second condensate. The liquid from the second condenser is supplied to the scrubber. In particular, the liquid from the second condenser is supplied to the scrubber separately from the first condensate and the first and second condensate are not mixed together. For instance, the liquid from the second condenser is supplied directly to the scrubber. This liquid comprises water and is preferably used as scrub liquid in the scrubber. In particular, the liquid from the second condenser (second condensate) is used as a part of the scrub liquid in the scrubber. The scrub liquid may further comprise acid. Because of the evaporative loss of water in the scrubber, make-up water is necessary in the scrubber, e.g. in the acid scrubber. The second condensate may be used to supply such water at least in part.

The condensate formed in the second condenser comprises $NH_3$. Therefore, preferably the scrubber is an acid scrub using acidic scrub liquid, so as to remove the $NH_3$. In the present invention the acid scrub is preferably very elegantly used not only for removing $NH_3$ from the off-gas from the finishing section, but also for processing the $NH_3$ in a part of the process condensate from the evaporation section in an energy efficient way.

The inventive process involves supplying said first condensate to a wastewater treatment section (WWT), preferably through absorbers. The WWT can also be described as a process condensate treatment section. For instance the first condensate, which comprises water, is used as absorption liquid in an absorber comprised in the urea plant, for absorbing $NH_3$ from a gaseous stream received by the absorber. It was found that advantageously the first condensate provides a sufficient amount of water for the operation of such absorbers.

Preferably the WWT comprises a hydrolyser and a desorber. Preferably the hydrolyser is configured for hydrolysing urea to ammonium carbamate and water. The hydrolyser uses e.g. HP steam.

Preferably the desorber is configured for desorption of $NH_3$ and $CO_2$. The desorber uses e.g. steam stripping with LP steam.

Preferably the WWT has an outlet for cleaned water (cleaned process condensate) and an outlet for a recycle stream comprising e.g. water vapor and ammonia and e.g. $CO_2$. The recycle stream is e.g. gaseous. The carbamate recycle solution is for instance supplied to a condenser of a recovery section, e.g. to a low pressure carbamate condenser, and then to the synthesis section. The lower loading of the WWT in the inventive process (in particular, less $NH_3$ received by the WWT) also yields a lower recycle stream from the WWT thereby advantageously decreasing the H/C ratio in the synthesis section (the H/C ratio is the molar ratio of water to $CO_2$ in the initial mixture, as described in Ullmann's Encyclopedia of Industrial Chemistry, chapter Urea (2010).

The cleaned water is for instance used as boiler feed water in order to raise steam. The steam is for instance used as heat transfer fluid in the urea plant.

The invention pertains to a urea production process using a first and a downstream second evaporator in an evaporation section, a finishing section and a scrubber for treating off-gas of the finishing section. Condensate from the condenser of the second evaporator is supplied to the scrubber, as described.

The invention also pertains to a urea production plant, preferably suitable for carrying out the urea production process of the invention, the plant comprising an evaporation section, a finishing section, a wastewater treatment section, and a scrubber. The evaporation section comprises a first evaporator and downstream thereof a second evaporator, and a first condenser and a second condenser. The first evaporator comprises an inlet for urea solution, an outlet for concentrated urea solution and an outlet for a first vapor. The second evaporator comprises an inlet for said concentrated urea solution, an outlet for urea melt and an outlet for second vapor. The finishing section comprises an inlet for said urea melt, an outlet for solid urea product and an outlet for off-gas and is configured for solidifying said urea melt into said solid urea product. The scrubber comprises an inlet for said off-gas and is configured for scrubbing said off-gas using scrub liquid. The first condenser comprises an inlet for said first vapor and an outlet for a first condensate. The second condenser comprises an inlet for said second vapor and an outlet for a second condensate. The wastewater treatment section comprises an inlet for said first condensate, and preferably a hydrolyser and a desorber. Hence, the plant comprises a (first) connection for said first condensate from said first condenser to said wastewater treatment section. The desorber is e.g. a steam stripper which uses steam as strip gas.

The plant comprises a (second) connection for the second condensate from the outlet of said the condenser to an inlet of the scrubber. In particular, this second connection is for supplying said second condensate to said scrubber separately from the first condensate.

Preferably, the scrubber comprises an inlet for acid connected to an external source of acid. The scrubber comprises an outlet for cleaned off-gas and an outlet for utilized scrub liquid. This outlet is preferably connected with an inlet of the evaporation section downstream (for urea solution) of the first evaporator. The outlet for utilized scrub liquid is for instance connected with an inlet of the second evaporator or e.g. to the supply line from the first evaporator to the second evaporator. The outlet for utilized scrub liquid is preferably connected with an inlet of the process side of the second evaporator, such that utilized scrub liquid is mixed with urea solution. Preferably the evaporation section comprises an inlet for an additive solution downstream (for urea solution) of the first evaporator, e.g. as an inlet of the second evaporator or as a supply line connected to the supply line for concentrated urea solution from the first to the second evaporator.

The urea plant and the evaporation section may optionally comprise additional evaporators upstream of the first evaporator, between the first and the second evaporator, and downstream of the second evaporator.

Preferences for the inventive plant apply equally for the inventive process. The plant is preferably suitable for the process of the invention. The inventive process is preferably carried out in the inventive plant.

In a preferred embodiment, the second condenser is a chilled condenser. The chilled condenser preferably uses a cooling medium that preferably is a compound or composition other than water, or for instance uses chilled water as cooling medium. Typically, the chilled condenser comprises a heat exchanger having a first side and a second side separated by at least a heat-exchanging wall. In a preferred embodiment, the vapor to be condensed is provided on the first side and chilled cooling medium is received on the second side. The first side and second side can, in addition to being separated by said wall, be separated by a further compartment for a heat transfer fluid such as water. The chilled cooling medium is typically supplied to an inlet of the condenser, at said second side, from a chiller. In the chiller, the cooling medium is chilled, for instance by at least 5° C. or at least 10° C. and/or to a temperature of less than 25° C. The chilled cooling medium at the inlet of the second condenser typically has a lower temperature than the cooling water that is used elsewhere in the urea plant and urea production process, e.g. at least 5° C. lower or at least 10° C. lower. Cooling water is for instance used in a first condenser connected to a first evaporator arranged upstream of the second evaporator. The preferred chilled cooling medium at the inlet of the second condenser typically has a temperature lower than the ambient temperature, e.g. at least 5° C. lower or at least 10° C. lower.

In some embodiments, the temperature of the cooling medium is for instance higher than 0° C. to avoid freezing of water in the process side of the condenser, and preferably temperature of cooling medium is at least 5° C., e.g. 5 to 10° C., e.g. at about 5° C.

The chiller is for instance a vapor-compression refrigeration system, comprising a compressor, condenser, expansion valve, and evaporator, connected by a loop for cooling medium. In a preferred embodiment, chilling of the cooling medium in the chiller involves subjecting the cooling medium received in the vapor phase from the cooling fluid side of the second condenser to compression to a higher pressure, condensation with heat withdrawal at said higher pressure, and expansion to a lower pressure to give chilled liquid cooling medium.

Advantageously, a chilled condenser can be used for efficiently transporting the second vapor from the evaporator to the condenser without using a booster ejector and without adding steam into the second vapor. In this way, the amount of liquid obtained from the second condenser advantageously remains small even if the second evaporator operates at a low pressure such as below 10 kPa.

Figure 2:
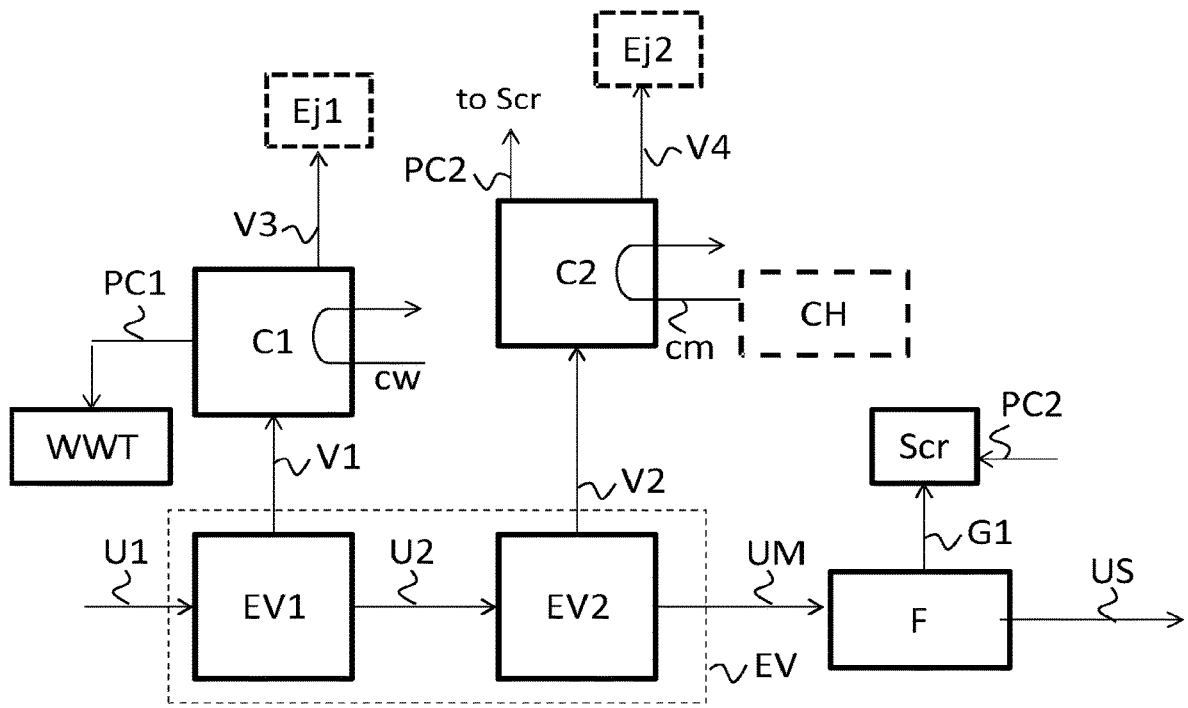
FIG. 2 schematically illustrates an example process and plant according to the invention.

FIG. 2 schematically illustrates an example process and plant according to the invention. The reference numbers indicate the same units as in FIG. 1 unless stated otherwise. The urea melt (UM) is sent to a finishing section (F) having an outlet for solid urea product (US) and an outlet for off-gas (G1). The off-gas is treated in a scrubber (Scr) which uses the second condensate (PC2) as scrub liquid. The second condenser (C2) has an outlet for liquid, namely the second condensate (PC2), which outlet is connected with an inlet of the scrubber (Scr) by a connection for sending the second condensate (PC2) directly to the scrubber (Scr). Optionally, the second condenser (C2) is a chilled condenser using a cooling medium supplied by a chiller (CH). In this embodiment preferably no booster ejector is used for transport of second vapor from the second evaporator to the second condenser.

Figure 3:
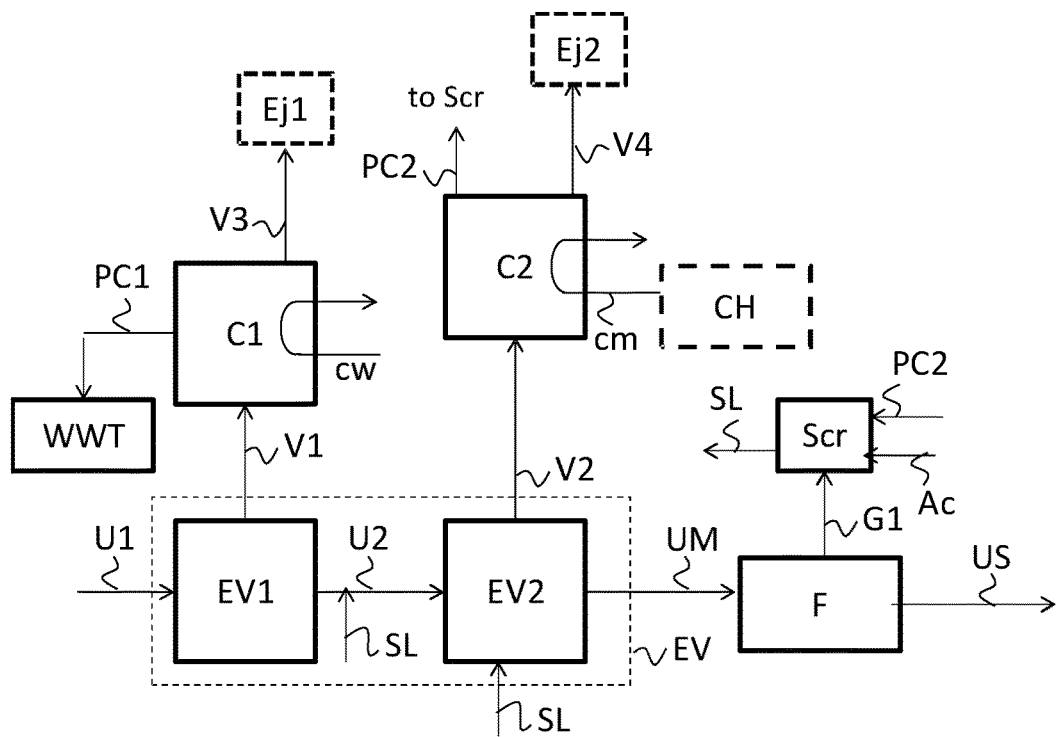
FIG. 3 schematically illustrates an example process and plant according to the invention.

FIG. 3 schematically illustrates an example process and plant according to the invention. The reference numbers indicate the same units as in FIG. 2 unless stated otherwise. The scrubber (Scr) is an acid scrubber using a supply of acid (Ac) and having an outlet for utilized scrub liquid (SL). The utilized scrub liquid (SL) is supplied to the evaporation section at a position downstream of the first evaporator. The utilized scrub liquid (SL) is e.g. supplied to the second evaporator (EV2) and/or to the supply line for the concentrated urea solution (U2).

Figure 4:
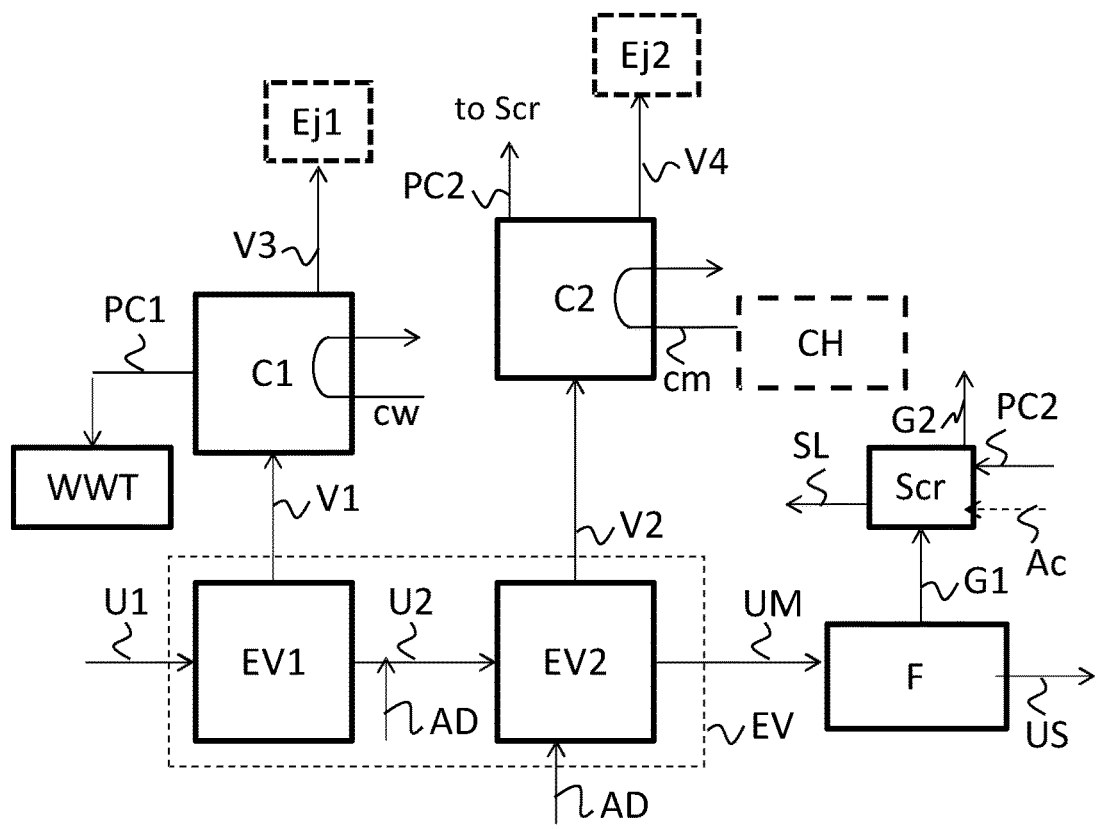
FIG. 4 schematically illustrates an example process and plant according to the invention.

FIG. 4 schematically illustrates an example process and plant according to the invention. The reference numbers indicate the same units as in FIG. 2 unless stated otherwise. The scrubber (Scr) has an outlet for utilized scrub liquid (SL) and is optionally an acid scrubber using a supply of acid (Ac). A liquid stream (AD) comprising water and one or more additives is supplied to the evaporation section (EV) at a position downstream (for urea solution) of the first evaporator (EV1). The liquid stream (AD) is for instance supplied to the transport line for concentrated urea solution (U2) or directly to the second evaporator (EV2). In this way, any traces of the additives in the second vapor (V2) do not contaminate the WWT. The water comprised in the liquid stream (AD) leaves the urea plant through the second vapor (V2), second (process) condensate (PC2) and through the outlet (G2) for cleaned off-gas of the scrubber (Scr) due to evaporation in the scrubber. In a preferred embodiment, the liquid stream (AD) is obtained as utilized scrub liquid from the scrubber and additives are added e.g. in solid form, to the scrubber, e.g. to the sump of the scrubber.

EXAMPLES

The invention will now be further illustrated in connection with the following examples which do not limit the invention.

Example 1

For an example urea plant based on a synthesis section of the $CO_2$ stripping type and with a granulator as finishing section, in a reference process 38.9 m³/h water was sent to the WWT whereas with the inventive process only 30.2 m³/h water was sent to the WWT. The yield was improved by about 0.4 wt. % since the urea in the second condensate was not hydrolysed but recycled, through utilized scrub liquid, into the solid urea product. The load to the first evaporation stage was about 120 t/h for both the reference and the inventive process. The load on the second evaporator was 99 t/h in the inventive process compared to 90 t/h in the reference process.

Example 2

For an example urea plant with a capacity of 2000 metric ton per day (MTPD) and a prilling tower, the WWT received 48 m³/h total water and 1716 kg/h $NH_3$ in a reference process and 30 m³/h total water and 1302 kg/h $NH_3$ in a process according to the invention where condensate from the second evaporator was sent to the scrubber for off-gas from the finishing section. The H/C ratio was 0.518 in the reference process and 0.509 in the inventive process. The HP stream consumption was 79 ton/h in the reference process and 78 ton/h in the inventive process. However, the LP steam export was advantageously 25 ton/h in the inventive process compared to 14.5 ton/h in the reference process.

The invention claimed is:

1. A urea production process comprising:
   a) concentrating urea solution in a first evaporator of an evaporation section, to give concentrated urea solution and a first vapor,
   b) further concentrating said concentrated urea solution from said first evaporator in a second evaporator of said evaporation section, to give a urea melt and second vapor,
   c) solidifying said urea melt in a finishing section giving solid urea product and off-gas,
   d) scrubbing said off-gas in a scrubber,
   e) condensing said first vapor in a first condenser to give a first condensate,
   f) condensing said second vapor in a second condenser to give a second condensate,
   g) supplying said first condensate to a wastewater treatment section, and
   h) separately supplying said second condensate to said scrubber, wherein said second condensate is used as scrub liquid in said scrubber, wherein said scrubber additionally uses an acid scrub liquid.

2. A urea production process according to claim 1, wherein said acid scrub liquid comprises nitric acid or sulphuric acid.

3. A urea production process according to claim 1, wherein said wastewater treatment section comprising a hydrolyser and a desorber.

4. A urea production process according to claim 1, wherein said finishing section is a prilling tower.

5. A urea production process according to claim 1, wherein said finishing section is a granulator.

6. A urea production process according to claim 1, wherein the urea melt from the second evaporator comprises less than 0.1 wt. % moisture.

7. A urea production process according to claim 1, wherein said scrubbing gives cleaned off-gas and utilized scrub liquid comprising urea, wherein the process further comprises supplying the utilized scrub liquid to the second evaporator.

8. A urea production process according to claim 1, wherein the utilized scrub liquid is added to the concentrated urea solution downstream of the first evaporator.

9. A urea production process according to claim 1, wherein the second evaporator operates at 130-140° C. and at a pressure of less than 15 kPa, and wherein the first evaporator gives a concentrated urea solution with at least 90 wt. % urea including biuret at the outlet and operates with a temperature of at least 120° C.

10. A urea production process according to claim 1, wherein a liquid stream comprising water and one or more additives is supplied to the evaporation section downstream for urea solution of the first evaporator.

11. A urea production process according to claim 10, wherein the liquid stream comprising one or more additives is mixed with the concentrated urea solution in the transport line between the first and second evaporator, or is supplied to an inlet of the second evaporator, and the solid urea product comprises the one or more additives in amount of at least 0.10 wt. % based on total weight of additives and total weight of solid urea product.

12. The urea production process of claim 10, wherein the one or more additives is an aqueous solution.

13. A urea production system comprising an evaporation section, a finishing section, a wastewater treatment section, and a scrubber, wherein the evaporation section comprises a first evaporator and downstream thereof a second evaporator, and a first condenser and a second condenser, wherein
   a) said first evaporator comprises an inlet for urea solution, an outlet for concentrated urea solution and an outlet for a first vapor,
   b) said second evaporator comprises an inlet for said concentrated urea solution, an outlet for urea melt and an outlet for second vapor,
   c) said finishing section comprises an inlet for said urea melt, an outlet for solid urea product and an outlet for off-gas and is configured for solidifying said urea melt into said solid urea product, d) said scrubber comprises an inlet for said off-gas and is configured for scrubbing said off-gas using scrub liquid,
e) said first condenser comprises an inlet for said first vapor and an outlet for a first condensate,
f) said second condenser comprises an inlet for said second vapor and an outlet for a second condensate,
g) said wastewater treatment section comprises an inlet for said first condensate, and
h) the plant comprises a connection for said second condensate from said outlet of said second condenser directly to an inlet of said scrubber.

14. A urea production system according to claim 13, wherein said wastewater treatment section comprising a hydrolyser and a desorber.

* * * * *